(12) United States Patent
Clement et al.

(10) Patent No.: US 7,096,714 B2
(45) Date of Patent: Aug. 29, 2006

(54) VOLATILE SIGNATURE DETECTOR AND ASSOCIATED METHODS

(75) Inventors: Jean-Luc Clement, Meudon (FR); Francoise Farnarier, Marseilles (FR); Florence Marquis, Pont et Massene (FR); Bernard Boeuf, Cabries (FR)

(73) Assignee: Centre National de la Recherche Scientifique, Paris Cedex (FR)

( * ) Notice: Subject to any disclaimer, the term of this patent is extended or adjusted under 35 U.S.C. 154(b) by 31 days.

(21) Appl. No.: 10/473,125

(22) PCT Filed: Mar. 27, 2002

(86) PCT No.: PCT/FR02/01065

§ 371 (c)(1),
(2), (4) Date: Mar. 9, 2004

(87) PCT Pub. No.: WO02/077636

PCT Pub. Date: Oct. 3, 2002

(65) Prior Publication Data

US 2004/0134273 A1  Jul. 15, 2004

(30) Foreign Application Priority Data

Mar. 27, 2001 (FR) .................................. 09 04079

(51) Int. Cl.
*G01N 33/497* (2006.01)
(52) U.S. Cl. .................................................... 73/23.3
(58) Field of Classification Search .................. 73/23.3
See application file for complete search history.

(56) References Cited

U.S. PATENT DOCUMENTS 3,649,199 A * 3/1972 Littlejohn ................... 436/178
3,676,072 A * 7/1972 Krivis .......................... 436/93
4,542,640 A   9/1985 Clifford
5,495,744 A * 3/1996 Ueda et al. ................. 73/1.07
5,571,401 A   11/1996 Lewis et al.
6,067,167 A * 5/2000 Atkinson et al. ........... 356/437

FOREIGN PATENT DOCUMENTS

| DE | 19607646 A1 * | 9/1997 |
|----|---|---|
| EP | 0 021 518 | 1/1981 |
| FR | 2 776 074 | 9/1999 |
| WO | WO 00 78204 | 12/2000 |
| WO | WO 01 13087 | 2/2001 |

OTHER PUBLICATIONS

Manolis, Anthony et al. "The detection of D9-tetrahydrocannabinol in the breath of human subjects" Clinical Biochemistry (1983), vol. 16(4), pp. 229-233.*
Engisch, Bob "Motorists May Face Dope Tests", dated May 13, 1998, at http://www.marijuananews.com/marijuananews/cowan/australian_motorists_may_face_ca.htm.*

* cited by examiner

*Primary Examiner*—Michael Cygan
(74) *Attorney, Agent, or Firm*—Young & Thompson

(57) ABSTRACT

A detector (D) for detecting the volatile signature of one or more substances, e. g. alcohol and/or cannabis, on the breath (MG) of a consumer (P), using several sensors (CT1, CT2, CT3). The sensors can comprise semi-conductors or conductive polymers. The inventive detector is equipped with a filter (F) to remove nuisance substances, e. g. water vapour, which mask the signature. The detector is advantageously portable and can be used to perform a test to evaluate (E) the consumption of a substance by the driver of a motor vehicle in relation to a reference level (N). A network of formal neurones (RN) is used to generate a database (DB) that is used to calibrate the detector.

15 Claims, 2 Drawing Sheets

VOLATILE SIGNATURE DETECTOR AND ASSOCIATED METHODS

The present invention relates to a detector for a substance's volatile signature, for example a cannabis signature in the breath of a smoker. It also relates to a method for the calibration of the detector, a method for implanting sensors therein and a method for detecting and assessing a molecule of the substance with such a detector.

Several types of detectors are known, for determining the presence of a molecule or of a set of molecules in a gaseous mixture. Certain of these detectors use specialized sensors and these sensors are sometimes disposable.

One detector of the specialized type is, for example, an ethyl test (or Alcootest®) which uses as sensor, crystals which react chemically with ethyl vapours contained in the breath. This reaction is irreversible and the detector is disposable.

There are also permanent sensors used for the detection of volatile compounds in gaseous phase, for example, in the safety field for detecting the presence of noxious or pollutant gases, for example carbon monoxide in the air. Certain of these sensors are semi-conductors or conductive polymers. They are also used in electronic noses for the detection of aromatic compounds. The semi-conductor sensors comprise a sensitive zone constituted by a semi-conductor material in a thin layer and maintained at an operating temperature, for example 350° C., by a heating resistor. The adsorption of certain components of the gas at the surface of the semi-conductor material causes the conductivity of the latter to vary. Measurement of the variation in conductivity makes it possible to detect the presence of the gas and to assess its concentration. For the semi-conductor material, it is possible to use a tin oxide crystal ($SnO_2$ for example), which can be doped by the addition to the crystal lattice of atomic compounds liable to modify the sensor's response. The conductive polymer sensors include a sensitive zone constituted by a network of conductive polymers, the conductivity of which is measured when they are in contact with the gaseous mixture. The polymer sensors moreover have the advantage of operating at ambient temperature and of being very small in size, for example thirty-two sensors over a few square millimetres.

There are also other types of sensors known for the detection of volatile compounds in gaseous phase, which are piezo-electric crystals and surface acoustic wave resonators.

In order to use "electronic noses", i.e. the sensors of aromas, a sample is taken, for example a perfume, which is introduced into a sampling cell. The sample is then analyzed simultaneously by a group of non-specific sensors, i.e. non-specialized in the detection of certain molecules. These sensors are of different sensibility or types. The responses of these sensors are then processed in order to provide a signature (or fingerprint) displayed on a computer. The signature is then compared to reference sample signatures in order to deduce the composition of the sample. However, this equipment is heavy, expensive laboratory equipment, and requires a high level of competence on the part of its users.

For example, semi-conductor sensors used in noses can be sensitive to gases in general, to propane and butane, to methane, propane and butane, to organic solvents (alcohol, toluene, xylene etc.), and the semi-conductor material of a sensor can form a plane or a tube.

In particular, for the semi-conductor sensors and the polymer sensors, it is important to take account of several internal parameters capable of influencing the quality of the analysis by the detector. One parameter is the response time necessary for an optimal response of the sensor starting from a stable initial state, the base line, and linked to an adsorption time. The base line is the value of the resistance of the sensor placed in a gaseous mixture considered as neutral, for example in air in the pure state. Another parameter is a reconditioning time for the sensor, i.e. its return to its base line after the analysis. Another parameter is also a risk of saturation of the sensors if the concentration of the adsorbable molecules is too high. The accuracy of the operating temperature and the accuracy in the production of the sensor also have a significant influence on the quality of the analysis.

It also appears that external conditions of the analysis also influence the reliability of the analysis by the detector. Thus, it is not easy to determine the base line of an apparatus which must be able to analyse breath in all types of environments, for example as different as a town and the seaside. The presence in the gaseous mixture of certain molecules or of certain compounds can also influence the analysis. Breath is a particular gaseous mixture owing to its strong water vapour content. Thus, detection of the signature of cannabis in the breath of a smoker can be masked by water molecules, therefore by water vapour with which the breath is saturated. In fact, the water vapour generally rapidly saturates the sensors which are then no longer functional. The high level of sensitivity of sensors to certain molecules, for example the alcohols, can also mask the signature of the product to be detected.

The behaviour of an operator, for example a driver, can be affected by substances that he has absorbed. This represents a danger in the accomplishment of hazardous tasks. Only the consumption of alcohol is generally controlled. However, certain studies in the United States have made it possible to establish that the consumption of cannabis was a cause of one-third of road accidents; it is THC which blocks the functioning of certain neurons, the anandamide neurons. Other drugs or medicaments can also affect behaviour. It is to be noted that users of other drugs are often also cannabis users. Cannabis is thus a tracer for the detection of users of drugs other than cannabis, in as much that the persistence time in the body of compounds originating from the consumption of cannabis is several days.

Whilst in a number of countries there is a call for the legalisation of cannabis use, and there is moreover a growing awareness of the effects of certain substances on behaviour, there is a lack of tools for monitoring and/or assessing the consumption of such substances, for example by a car driver. Known means make it possible to detect and assay substances such as drugs or medicaments in mixtures in liquid solution, and therefore most of the time these means are better adapted to laboratory analyses. Yet, before carrying out more precise analyses of the products originating from these substances and present in the organism, for example using a blood sample, it is important to be able to carry out a non-invasive test, such as the ethyl test. Breath analysis is experienced as being the least invasive and the best complied with.

The objective of the invention is therefore to propose a device which is simple to use and to maintain, reliable, inexpensive, and which can if necessary be reduced in size, in order to assess the presence and/or the concentration of a substance in the breath of a human or of another animal, without the disadvantages mentioned previously.

According to the invention, in order to detect a substance's volatile signature in the breath, a detector is used which comprises:

a group of gas sensors;

means for storing the calibration coefficients of the detector; and, means for combining responses of the sensors with the coefficients, these same means thus making it possible to supply information on the presence of said substance.

Such a detector makes it possible in particular to detect a substance previously inhaled by the animal, for example by a human being smoking.

The detector can moreover comprise means for filtering the breath. In particular, these means for filtering can make it possible to eliminate from the breath a large part, or all, of certain gases or certain molecules which could disturb the detection or mask the signature sought. The breath can thus be filtered in order to trap water vapour or alcohol vapours contained in the breath.

Advantageously, a detector according to the invention comprises a number of sensors comprised between 4 and 25. This number varies according to the type of sensors used and according to the type of signature sought. Among the sensors, it is therefore possible to use certain ones, a sensitive zone of which mainly comprises a semi-conductor substance and/or others, a sensitive zone of which mainly comprises a conductive polymer.

The memory used to store the calibration coefficients is preferably comprised in an electronic memory which can be changed simultaneously in the group of sensors. For high-cost sensors, it may be preferable to change only one or certain sensors in the group, to carry out a new calibration and to modify the memory coefficients. It is also possible to periodically calibrate a group of sensors, certain characteristics of which vary as a function of time, and if the cost of this group justifies a periodic calibration rather than replacement by a new group.

A detector according to the invention can be designed to detect the signature of an alcoholic substance or of a substance derived from cannabis. It can be also designed to discriminate between, and recognize the signatures of several substances, simultaneously or not simultaneously. It can also be portable.

A method for calibrating a detector according to the invention comprises the following steps:

each of the sensors in the group is calibrated;

for each sensor and for each substance of which the signature is to be detected, coefficients are determined from a database, to be applied to the responses of said sensors;

a memory is associated with the group of sensors;

the coefficients are entered into the memory;

In order to create the database, it is possible:

to define types of sensors to be used in the detector;

for groups of sensors of a different range in each type, to learn, using a neural network, to detect the signature under variable-mix conditions; and, to store data from this learning process.

Other features and advantages of the invention will also become clear from the description hereafter, which relates to non-limitative examples.

Figure 1:
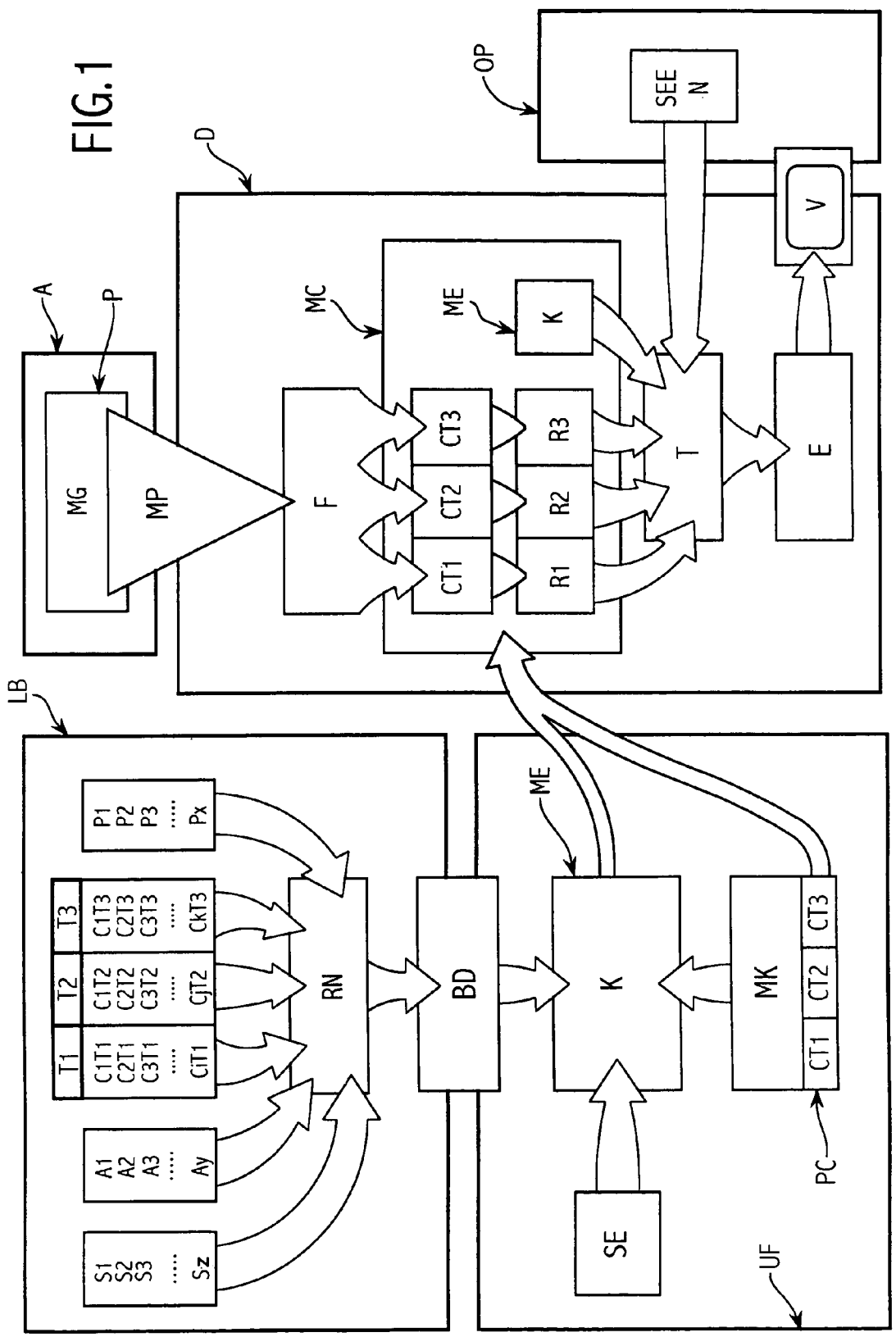
FIG. 1 is a diagrammatic and simplified representation of possible stages for the adjustment and use of a detector according to the invention.

The detector D, the operation of which is shown diagrammatically in FIG. 1, is provided in order to detect the signature of one or more substances SDD to be detected. The adjustment of such a detector starts in the laboratory LB. First an area of operation is determined for the detector. Here it is provided to control the consumption by car drivers of substances liable to modify their driving behaviour, for example alcohol and cannabis. For this purpose the choice is made to sample a gaseous mixture which is the breath of a driver, and to rapidly test it by means of the detector D. If this test is positive, i.e. if the substance is detected and particularly if its count is above a count N beyond which driving is considered as dangerous, a more precise analysis can be carried out, for example of a blood sample.

However, it is not enough to take into account only the substances sought but also other substances in the driver's breath. Thus, cannabis is used in combination with tobacco; it is therefore important to distinguish between the tobacco user alone, and those having used cannabis. It must be possible, from substances S1–Sz comprising several types of alcohol, several types of tobacco, several types of cannabis and other associated substances, to discriminate between an alcohol and a cannabis signature. Other parameters can also influence the analysis, in particular, the atmosphere A breathed by the driver P, i.e. the ambient air, but also the body of the driver himself. An important parameter is also the variability of the sensors used. This means that, in order to keep detector costs down, it is important to use standard commercial sensors and this can lead to acceptance of a certain variability in the individual response of each sensor to a given stimulus.

Figure 2:
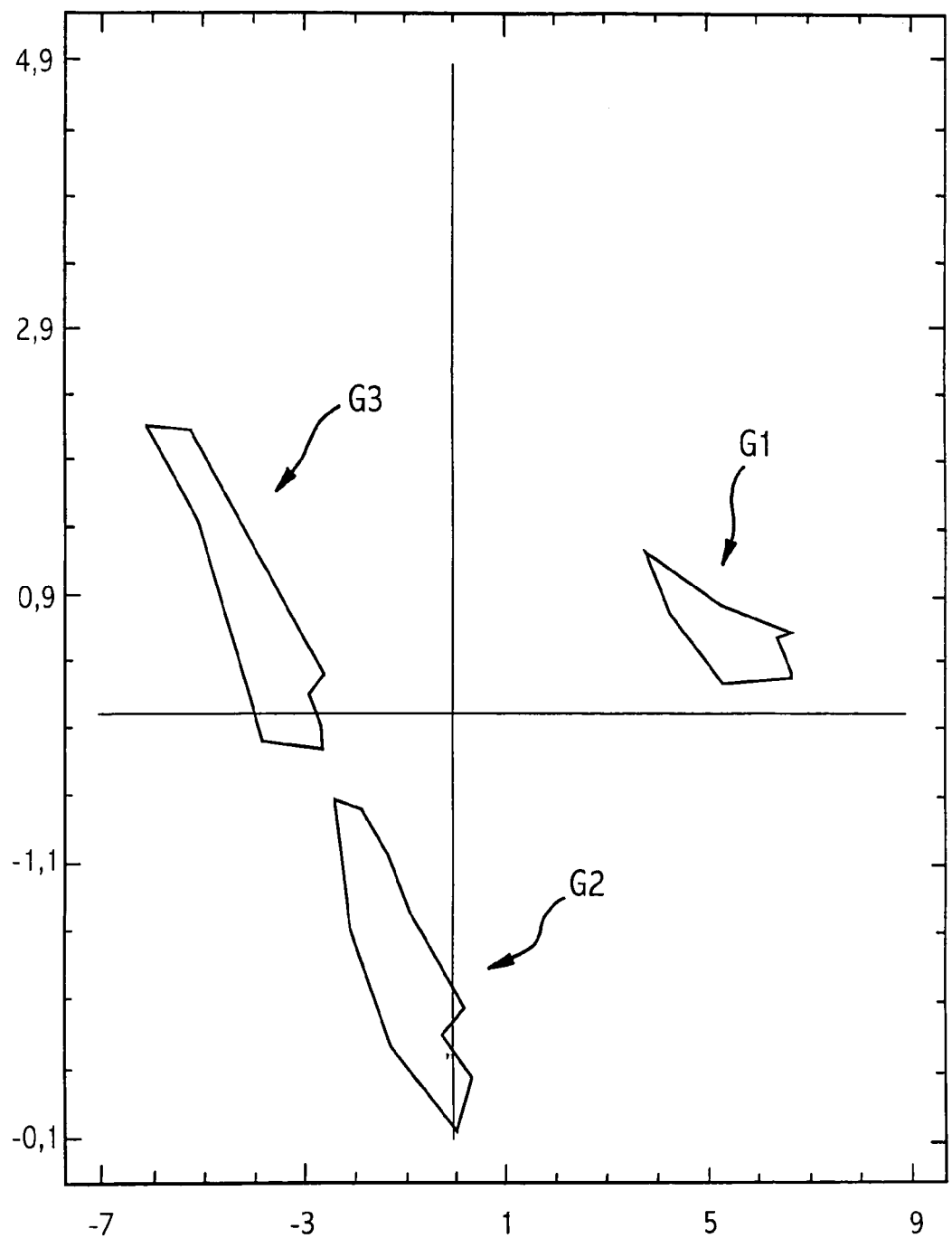
FIG. 2 is a representation of the responses of sensors projected according to two axes following a main component analysis.

FIG. 2 is a representation with a main component analysis, i.e. a plane projection of a space comprising a high number of dimensions. Thus, for a detector comprising n sensors, a different axis is assigned to a representation of the responses of each of the n sensors. All of these n axes defines a space with n dimensions in which a response of the detector during a detection is represented by coordinates which are the individual responses of the sensors for this same detection. Then in this space two axes are chosen such that the detector-response projections of each of these axes have a maximal dispersion. Detector-response projections, in the plane defined by these two axes, form a main component representation thereof.

In the study illustrated in FIG. 2, simultaneous responses of sensors form, for variable parameters, point clouds. Thus, the coordinates originating from the responses of the sensors define groups of perceptibly distinct measurements for gaseous mixtures to be discriminated between. The points are mainly grouped into three clouds G1, G2, G3. The cloud G1 corresponds to the analysis of a gaseous mixture MG which is constituted exclusively by air; this is the base line. The cloud G2 corresponds to the analysis of air containing only tobacco smoke. The cloud G3 corresponds to the analysis of air containing cannabis smoke mixed with tobacco, the relative humidity level of which is maintained below 20%. These clouds are sufficiently distinct to consider the sensors as discriminating for cannabis. This study was carried out with smoking machines.

Thus, a substance's signature is assimilated to possible combinations for responses of the sensors. It is not important to know which molecules originating from the substance react with a sensor. It can be also a molecule which did not originate from the substance but, for example, which is emitted in the breath of a person in reaction to the absorption of this substance. The signature is therefore an abstract representation deduced from volatile elements originating, for example, from the consumption of the substance sought.

In the example of FIG. 1, when carrying out a study as illustrated in FIG. 2, three types of sensors T1, T2, T3 were chosen. Thus groups of three sensors were constituted. Each group PC is constituted by a unique combination of three sensors each chosen from one type. These sensors, combined in the presence of the breath to be analyzed, make it possible to distinguish between the substances S1–Sz to be discriminated. It is possible in the laboratory to reproduce on a computer screen, a two-dimensional space of the type of that in FIG. 2 and to identify therein the position of points corresponding to an analysis. A user can then deduce from these the assessment of the presence of a substance. However, as has been said, this requires a good deal of equipment, and a certain expertise on the part of the user.

During the development of the detector within the laboratory LB, groups of three sensors, each of a different type, are constituted, from C1T1–CiT1 sensors of a first type T1, from C1T2–CjT2 sensors of a second type T2 and C1T3–CkT3 sensors of a third type T3. During successive sessions each of these groups is placed in the presence of breath originating from different subjects P1–Px having breathed different atmospheres A1–Ay and consumed different substances or different mixtures of substances chosen from the substances S1–Sz to be detected. The subjects can be physical persons for substances S1–Sz to be detected, not presenting any health risk to these persons, or machines, for example smoking machines. The successive sessions make possible the gradual learning of the assessment of the presence of the substances or mixtures of substances in breath as a function of the groups used. This learning is carried out using a neural network RN i.e. a processing of the signal which mimics the learning of the human brain. This learning is continued until the assessment is sufficiently precise. In laboratory tests it was found that after less than 150 learning cycles, a substance was not recognized in less than one per cent of cases, which means that there is a detection error. After fewer than 2000 cycles this error was less than one per thousand. The knowledge resulting from the learning process is then stored in the form of a database BD. This database must allow the calibration of any group PC of sensors CT1, CT2, CT3 intended to equip the detector D.

A capture module MC intended to equip the detector is produced in a production unit UF. The three sensors CT1, CT2, CT3 are respectively of the types T1, T2, T3. The respective range of each of the sensors is determined, i.e. the response of each of the sensors respectively to a known stimulus, chosen in order to calibrate said sensor, is observed using calibration means MK. The choice is made from the substances S1–Sz having served to establish the database of the substances SE which can be assessed by the sensor when it is equipped with the capture module MC. In the example, the assessable substances are alcohol and cannabis. The database BD is then consulted in order to determine coefficients K from the ranges of the sensors and from the chosen assessable substances. These coefficients are stored in an electronic memory ME. They are specific to the group of sensors and to the chosen assessable substances. The electronic memory is therefore integrated jointly with the group PC of sensors within the detection module MD. The module is then implanted in the detector D, either during the manufacture of the detector, or during replacement of a previous detection module. The module MC is changeable. It can be changed when a sensor is defective or if it is desired to be able to assess new substances SE. The coefficients K being strictly linked to a given group of sensors PC and to given assessable substances SE, it is advisable to change the module MC in its entirety, i.e. to simultaneously change all of the sensors CT1, CT2, CT3 and the associated memory ME.

During the use of the detector D by an operator OP, for example a police officer, the latter chooses one or more substances to be assessed SEE, for example cannabis, from the assessable substances SE, i.e. alcohol and cannabis. Moreover he chooses the level N, corresponding to a concentration of cannabis in the body of the inspected driver P, beyond which driving is dangerous, i.e. cannabis intoxication, and beyond which the driver is presumed to be in breach of a safety regulation.

The operator OP takes a breath sample MG from the driver P using sampling means MP. This breath is then filtered via a filter F in order to eliminate excess water vapour, before being brought into contact with the sensors CT1, CT2, CT3. This filter can be a molecular sieve. Upon contact with the breath, the sensors CT1, CT2, CT3 respectively emit responses R1, R2, R3. These responses are processed by a processing unit T in combination with the coefficients K of the memory ME and the choices of the substance to be assessed SEE and the level N. The processing unit deduces from these an assessment E which is transmitted to display means V for the operator OP.

Of course, the invention is not limited to the examples which have just been described and a number of developments can be made to these examples without exceeding the scope of the invention.

Thus, the operator may not have the choice of the substance SEE to be assessed, nor of the level N. Nor is a detector according to the invention limited to the detection of cannabis or alcohol intoxication. It can serve to detect pollutants in the atmosphere using types of non-specialized sensors having learned to recognize these pollutants. Instead of sensors having a strong variability, it is also possible to use sensors, the production characteristics of which are very stable if the cost of production is acceptable with regard to the desired use. The number of sensors in the same group can be less than or more than three. In particular in the case of the use of polymer sensors it is preferable to have a larger number of sensors. The number of sensors can also be a function of the number of substances to be discriminated between, or of a substance having a signature less legible than that of other substances.

The invention claimed is:

1. A detector (D) of a substance derived from cannabis's volatile signature (SEE) in breath (MG), comprising:
   a group (PC) of gas sensors (CT1, CT2, CT3);
   means for storing (ME) calibration coefficients (K) of the detector; and
   means (T) for combining the responses of the sensors with said coefficients and for supplying information on the presence of said substance derived from cannabis.

2. A detector according to claim 1, characterized in that it moreover comprises means (F) for filtering the breath.

3. A detector according to claim 2, characterized in that the filtering means include a filter for trapping water vapour contained in the breath.

4. A detector according to claim 2, characterized in that the filtering means include a filter for trapping the alcohol vapours contained in the breath.

5. A detector according to claim 2, characterized in that the filtering means comprise a molecular sieve.

6. A detector according to claim 1, characterized in that it comprises a number of sensors comprised between 4 and 32.

7. A detector according to claim 1, characterized in that certain of the sensors include a sensitive zone constituted mainly by a semi-conductor substance and/or a sensitive zone constituted mainly by a conductive polymer.

8. A detector according to claim 1, characterized in that the memory is comprised in an electronic memory and that said electronic memory can be changed simultaneously for the group of sensors.

9. A detector according to claim 1, characterized in that it moreover comprises means for discriminating between and recognizing in the breath, the signatures of the substance derived from cannabis and the signature of several substances.

10. A portable device comprising a detector according to claim 1.

11. A method for calibrating a detector according to claim 1, comprising the following steps:
   each of the sensors in the group is calibrated;
   for each sensor and for each substance of which the signature is to be detected, coefficients are determined from a database (BD), to be applied to the responses (R1, R2, R3) of said sensors;
   a memory is associated with the group of sensors;
   the coefficients are entered into the memory;
   in order to create the database, types (T1, T2, T3) are first defined for the sensors used in the detector, then data are stored, originating from the learning, using a neural network (RN), of the detection of the signature under variable-mix conditions and for groups of sensors of different ranges in each type.

12. A method for implanting sensors into a detector according to claim 1, characterized in that a group of sensors and an electronic memory associated with said group are implanted simultaneously.

13. A method for detecting, in breath, a volatile signature for a substance derived from cannabis, with a detector according to claim 1, characterized in that the breath is filtered in order to trap a nuisance molecule contained in the breath, and the detection is carried out in the filtered breath.

14. A method according to claim 11, characterized in that it is used to detect a sought molecule originating from the substance derived from cannabis.

15. A method according to claim 11, characterized in that in order to assess the concentration of the molecule originating from the substance derived from cannabis, the signature of the substance derived from cannabis in the breath at least partially originating from said substance derived from cannabis is assessed.

* * * * *